(12) United States Patent
Liu et al.

(10) Patent No.: US 10,729,373 B2
(45) Date of Patent: Aug. 4, 2020

(54) FAN, AND CONTROL SYSTEM AND METHOD THEREFOR

(71) Applicant: GD MIDEA ENVIRONMENT APPLIANCES MFG CO., LTD., Zhongshan (CN)

(72) Inventors: Jinquan Liu, Zhongshan (CN); Xinyun Pan, Zhongshan (CN)

(73) Assignees: GD MIDEA ENVIRONMENT APPLIANCES MFG CO., LTD., Zhongshan (CN); MIDEA GROUP CO., LTD., Foshan (CN)

(*) Notice: Subject to any disclaimer, the term of this patent is extended or adjusted under 35 U.S.C. 154(b) by 107 days.

(21) Appl. No.: 16/116,702

(22) Filed: Aug. 29, 2018

(65) Prior Publication Data

US 2018/0368754 A1 Dec. 27, 2018

Related U.S. Application Data

(63) Continuation of application No. PCT/CN2016/103619, filed on Oct. 27, 2016.

(30) Foreign Application Priority Data

Feb. 29, 2016 (CN) .......................... 2016 1 0115456

(51) Int. Cl.
*F04D 15/00* (2006.01)
*A61B 5/00* (2006.01)
(Continued)

(52) U.S. Cl.
CPC .......... *A61B 5/4809* (2013.01); *F04D 27/004* (2013.01); *F04D 27/007* (2013.01);
(Continued)

(58) Field of Classification Search
CPC .. F04D 27/004; F04D 27/008; F05D 2270/02; F05D 2270/30; A61B 5/4809; F24F 11/66
See application file for complete search history.

(56) References Cited

U.S. PATENT DOCUMENTS

2009/0107498 A1  4/2009 Plattner et al.
2015/0009045 A1* 1/2015 Proud .................... H04W 4/80
                                              340/870.09
(Continued)

FOREIGN PATENT DOCUMENTS

CN       104235997 A    12/2014
CN       104728146 A     6/2015
(Continued)

OTHER PUBLICATIONS

GD Midea Environment Appliances MFG Co Ltd. et al., Extended European Search Rport, EP16892349.8, dated Oct. 4, 2019, 7 pgs.
(Continued)

*Primary Examiner* — Ninh H. Nguyen
(74) *Attorney, Agent, or Firm* — Morgan, Lewis & Bockius LLP

(57) ABSTRACT

A fan, and a control system and method therefor, wherein the system comprises a wearable device (100) and a fan (200). The fan (200) communicates with the wearable device (100). The wearable device (100) is used for detecting body parameters of a user to determine whether the user falls asleep, generating a sleep wind mode instruction to the fan (200). The fan (200) enters a sleep wind mode after receiving the sleep wind mode instruction, obtains a sleep wind control curve, and adjusts operating parameters according to the sleep wind control curve. The fan control system can adjust the running gear of the fan according to the sleep wind control curve after the user falls asleep, and avoids interfer-
(Continued)

---

- S1: detecting, by the wearable device, a body parameter of a user to determine whether the user enters a sleeping state
- S2: generating a sleeping wind mode instruction when the user enters the sleep state
- S3: controlling the fan to enter a sleeping wind mode according to the sleeping wind mode instruction, obtaining a sleeping wind control curve after the fan enters the sleeping wind mode, and adjusting an operation parameter according to the sleeping wind control curve ence factors, thereby improving the control precision of the fan and improving user experience.

17 Claims, 3 Drawing Sheets

(51) Int. Cl.
   *F04D 27/00* (2006.01)
   *F24F 11/66* (2018.01)
(52) U.S. Cl.
   CPC ........ *F04D 27/008* (2013.01); *F05B 2270/32* (2013.01); *F24F 11/66* (2018.01)

(56) References Cited

U.S. PATENT DOCUMENTS

| | | | |
|---|---|---|---|
| 2015/0182164 A1* | 7/2015 | Utter, II | A61B 5/0022 600/301 |
| 2016/0100696 A1* | 4/2016 | Palashewski | A61B 5/4809 700/90 |
| 2017/0333667 A1* | 11/2017 | Tucker | A61B 5/4836 |

FOREIGN PATENT DOCUMENTS

| | | |
|---|---|---|
| CN | 104914834 A | 9/2015 |
| CN | 105317722 A | 2/2016 |
| CN | 105318503 A | 2/2016 |
| CN | 105650020 A | 6/2016 |
| JP | 2015113727 A | 6/2015 |
| JP | 6213936 B2 | 10/2017 |
| WO | WO2015141109 A1 | 9/2015 |

OTHER PUBLICATIONS

Notice of Reasons for Refusal, JP2018545359, dated Sep. 3, 2019, 12 pgs.
International Search Report, PCT/CN2016/103619, dated Jan. 23, 2017, 15 pgs.
GD Midea Environment Appliances MFG Co Ltd., Fifth Notification of Office Action, CN201610115456.1, dated Oct. 16, 2018, 29 pgs.

\* cited by examiner

FAN, AND CONTROL SYSTEM AND METHOD THEREFOR

CROSS REFERENCE TO RELATED APPLICATIONS

This application is a continuation application of PCT Patent Application No. PCT/CN2016/103619, entitled "FAN, AND CONTROL SYSTEM AND METHOD THEREFOR" filed on Oct. 27, 2016, which claims priority to Chinese Patent Application No. 201610115456.1, entitled "FAN, AND CONTROL SYSTEM AND METHOD THEREFOR," filed on Feb. 29, 2016, all of which are hereby incorporated by reference in their entirety.

TECHNICAL FIELD

The present disclosure relates to a household appliance technology field, and more particularly to a fan control system, a fan, and a control method of a fan.

BACKGROUND

At present, the fan is gradually developing in the direction of intelligence. During the operation of the fan, a wind speed of the fan can be automatically adjusted.

In the related art, the wind speed of the fan is adjusted in real time by acquiring temperature of human body. However, due to factors such as detection accuracy and real-time detection, the control accuracy of the fan is relatively low, which affects user experience.

SUMMARY

Embodiments of the present disclosure seek to solve at least one of the problems existing in the related art to at least some extent.

Accordingly, a first objective of the present disclosure is to provide a fan control system, which may adjust an operation gear of the fan according to a sleeping wind control curve when a user enters a sleeping state, without interference factors, thus improving control accuracy of the fan, and improving user experience.

A second objective of the present disclosure is to provide a fan.

A third objective of the present disclosure is to provide a control method of a fan.

To achieve the above objectives, a first aspect of embodiments of the present disclosure provides a fan control system, including a wearable device and a fan. The fan and the wearable device communicate with each other. The wearable device is configured to detect a body parameter of a user to determine whether the user enters a sleeping state, to generate a sleeping wind mode instruction when the user enters the sleeping state, and to send the sleeping wind mode instruction to the fan. The fan is configured to enter a sleeping wind mode after receiving the sleeping wind mode instruction, to obtain a sleeping wind control curve, and to adjust an operation parameter according to the sleeping wind control curve.

With the fan control system according to embodiments of the present disclosure, the wearable device detects the body parameter of the user to determine whether the user enters the sleeping state, generates the sleeping wind mode instruction when the user enters the sleeping state, and the sleeping wind mode instruction is sent to the fan, the fan enters the sleeping wind mode after receiving the sleeping wind mode instruction, the sleeping wind control curve is obtained, and the operation parameter is adjusted according to the sleeping wind control curve. Thereby, the system may adjust an operation gear of the fan according to the sleeping wind control curve when the user enters the sleeping state, without interference factors, thus improving control accuracy of the fan, and improving the user experience.

In addition, the fan control system according to above mentioned embodiments of the present disclosure may further include following additional technical features.

In an embodiment of the present disclosure, the fan operates at a preset gear when the fan does not receive the sleeping wind mode instruction.

In an embodiment of the present disclosure, the operation parameter comprises an operation gear and a rotation angle, the sleeping wind control curve is a curve representing a correspondence relationship between sleeping time periods and operation gears.

In an embodiment of the present disclosure, the sleeping wind control curve is generated based on a basic reference variable, the basic reference variable is a preset gear of the fan before the user enters the sleeping state.

In an embodiment of the present disclosure, the fan is further configured to rotate according to a preset rotation angle when the fan adjusts an operation gear according to the sleeping wind control curve.

In an embodiment of the present disclosure, the wearable device is configured to start a timer when detecting that the user wakes up from the sleeping state, to generate an exit instruction when a time period recorded by the timer reaches a preset time period, and to send the exit instruction to the fan, such that the fan exits the sleeping wind mode.

In an embodiment of the present disclosure, when communication connection between the wearable device and the fan is disconnected, the fan is automatically turned off; when the communication connection between the wearable device and the fan is re-established, the fan is automatically turned on.

In an embodiment of the present disclosure, the fan control system further includes a cloud server. The cloud server is configured to communicate with the fan, the fan is configured to send an operation parameter each time the fan enters the sleeping wind mode to the cloud server, the cloud server is configured to modify the sleeping wind control curve according to the operation parameter, and to send the modified sleeping wind control curve to the fan.

In an embodiment of the present disclosure, the wearable device is further configured to generate a wind speed adjusting instruction according to the body parameter of the user, and to send the wind speed adjusting instruction to the fan to adjust an outlet wind speed of the fan.

In an embodiment of the present disclosure, the fan includes: a communication module, configured to establish a communication connection with the wearable device; blades; a motor, configured to drive the blades to rotate; and a main control module, configured to control an operation mode of the fan, and to control a rotation speed of the motor according to the operation mode of the fan.

To achieve the above objectives, a second aspect of embodiments of the present disclosure provides a fan, including: a communication module, configured to establish a communication connection with a wearable device to receive a sleeping wind mode instruction sent by the wearable device, in which the wearable device is configured to detect a body parameter of a user to determine whether the user is in a sleeping state, and to generate the sleeping wind mode instruction when the user is in the sleeping state;

blades; a motor, configured to drive the blades to rotate; and a main control module, configured to control the fan to enter a sleeping wind mode when the communication module receives the sleeping wind mode instruction, to obtain a sleeping wind control curve, and to adjust an operation parameter of the fan according to the sleeping wind control curve.

With the fan according to embodiments of the present disclosure, communication connection with the wearable device is established by the communication module to receive the sleeping wind mode instruction sent from the wearable device, controls the fan is controlled by the main control module to enter the sleeping wind mode when the communication module receives the sleeping wind mode instruction, the sleeping wind control curve is obtained, and the operation parameter is adjusted according to the sleeping wind control curve. Thereby, the fan may adjust an operation gear of the fan according to the sleeping wind control curve when the user enters the sleeping state, without interference factors, thus improving control accuracy of the fan, and improving the user experience.

In addition, the fan according to above mentioned embodiments of the present disclosure may further include following additional technical features.

In an embodiment of the present disclosure, the communication module is further configured to receive a gear setting instruction sent from a remote control or the wearable device, the main control module is configured to control the fan to operate at a preset gear according to the gear setting instruction.

In an embodiment of the present disclosure, the operation parameter comprises an operation gear and a rotation angle, the sleeping wind control curve is a curve representing a correspondence relationship between sleeping time periods and operation gears.

In an embodiment of the present disclosure, the sleeping wind control curve is generated based on a basic reference variable, the basic reference variable is a preset gear of the fan before the user enters the sleeping state as a basic reference variable.

In an embodiment of the present disclosure, the main control module is further configured to control the fan to rotate according to a preset rotation angle when adjusting an operation gear according to the sleeping wind control curve.

In an embodiment of the present disclosure, when the wearable device is configured to start a timer when detecting that the user wakes up from the sleeping state, to generate an exit instruction when a time period recorded by the timer reaches a preset time period, and to send the exit instruction to the communication module, the main control module is configured to control the fan to exit the sleeping wind mode according to the exit instruction.

In an embodiment of the present disclosure, the main control module is configured to control the fan to turn off automatically when communication connection between the wearable device and the fan is disconnected; the main control module is configured to control the fan to turn on automatically when the communication connection between the wearable device and the fan is re-established.

In an embodiment of the present disclosure, the fan is configured to communicate with a cloud server through the communication module, and to send an operation parameter each time the fan enters the sleeping wind mode to the cloud server; the cloud server is configured to modify the sleeping wind control curve according to the operation parameter, and to send the modified sleeping wind control curve to the fan.

In an embodiment of the present disclosure, the wearable device is further configured to generate a wind speed adjusting instruction according to the body parameter of the user, and to send the wind speed adjusting instruction to the communication module, the main control module is configured to adjust a rotation speed of the motor according to the wind speed adjusting instruction to adjust an outlet wind speed of the fan.

To achieve the above objectives, a third aspect of embodiments of the present disclosure provides a control method of a fan. The fan communicates with a wearable device. The method includes: detecting, by the wearable device, a body parameter of a user to determine whether the user enters a sleeping state; generating a sleeping wind mode instruction when the user enters the sleeping state; and controlling the fan to enter a sleeping wind mode according to the sleeping wind mode instruction, obtaining a sleeping wind control curve after the fan enters the sleeping wind mode, and adjusting an operation parameter according to the sleeping wind control curve.

With the control method of a fan according to embodiments of the present disclosure, the wearable device detects the body parameter of the user to determine whether the user enters the sleeping state, the sleeping wind mode instruction is generated when the user enters the sleeping state, and the fan is controlled to enter the sleeping wind mode, the sleeping wind control curve is obtained after the fan enters the sleeping wind mode, and the operation parameter is adjusted according to the sleeping wind control curve. Thereby, the system may adjust an operation gear of the fan according to the sleeping wind control curve when the user enters the sleeping state, without interference factors, thus improving control accuracy of the fan, and improving the user experience.

In addition, the control method of a fan according to above mentioned embodiments of the present disclosure may further include following additional technical features.

In an embodiment of the present disclosure, the fan operates at a preset gear when the fan does not receive the sleeping wind mode instruction.

In an embodiment of the present disclosure, the operation parameter comprises an operation gear and a rotation angle, the sleeping wind control curve is a curve representing a correspondence relationship between sleeping time periods and operation gears.

In an embodiment of the present disclosure, the sleeping wind control curve is generated based on a basic reference variable, the basic reference variable is a preset gear of the fan before the user enters the sleeping state.

In an embodiment of the present disclosure, the method further includes: controlling the fan to rotate according to a preset rotation angle when adjusting an operation gear according to the sleeping wind control curve.

In an embodiment of the present disclosure, the method further includes: when the wearable device detects that the user wakes up from the sleeping state, starting a timer; when a time period recorded by the timer reaches a preset time period, generating an exit instruction by the wearable device, and sending the exit instruction to the fan, such that the fan exits the sleeping wind mode.

In an embodiment of the present disclosure, the method further includes: when communication connection between the wearable device and the fan is disconnected, controlling the fan to turn off automatically; when the communication connection between the wearable device and the fan is re-established, controlling the fan to turn on automatically.

In an embodiment of the present disclosure, the fan further communicates with a cloud server, and sends an operation parameter each time the fan enters the sleeping wind mode to the cloud server, and the cloud server modifies the sleeping wind control curve according to the operation parameter, and sends the modified sleeping wind control curve to the fan.

In an embodiment of the present disclosure, the method further includes: generating, by the wearable device, a wind speed adjusting instruction according to the body parameter of the user; and sending the wind speed adjusting instruction to the fan to adjust an outlet wind speed of the fan.

Additional advantages of embodiments of present disclosure will be given in part in the following descriptions, become apparent in part from the following descriptions, or be learned from the practice of the embodiments of the present disclosure.

DETAILED DESCRIPTION

Figure 1:
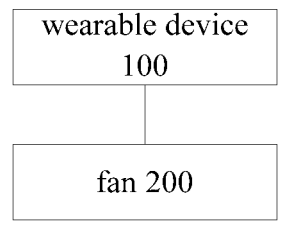
FIG. 1 is a block diagram illustrating a fan control system according to an embodiment of the present disclosure.

Reference will be made in detail to embodiments of the present disclosure. The embodiments described herein with reference to drawings are explanatory, illustrative, and used to generally understand the present disclosure. The embodiments shall not be construed to limit the present disclosure. The same or similar elements and the elements having same or similar functions are denoted by like reference numerals throughout the descriptions.

In the following, a fan and a control system and method thereof according to embodiments of the present disclosure will be described with reference to drawings.

FIG. 1 is a block diagram illustrating a fan control system according to an embodiment of the present disclosure. As illustrated in FIG. 1, the fan control system includes a wearable device 100 and a fan 200.

The wearable device 100 is configured to detect a body parameter of a user to determine whether the user enters a sleeping state, to generate a sleeping wind mode instruction when the user enters the sleeping state, and to send the sleeping wind mode instruction to the fan 200. The fan 200 is configured to enter a sleeping wind mode after receiving the sleeping wind mode instruction, to obtain a sleeping wind control curve, and to adjust an operation parameter according to the sleeping wind control curve.

In detail, in some embodiments of the present disclosure, the wearable device 100 may determine whether the user enters the sleeping state by detecting a current heart rate and exercise parameter information of the user. For example, the wearable device 100 may determine whether the user enters the sleeping state by detecting a heart rate and exercise parameter information in 20 minutes of the user. If it is determined that the user enters the sleeping state, the wearable device 100 generates the sleeping wind mode instruction, and sends the sleeping wind mode instruction to the fan 200. When a distance between the fan 200 and the wearable device 100 is relative small, for example, 10 meters, the fan 200 and the wearable device 100 may perform communication through Bluetooth, WiFi, and the like. After the fan 200 receives the sleeping wind mode instruction sent from the wearable device 100, the fan automatically enters the sleeping wind mode. The fan obtains the sleeping wind control curve, and adjusts the operation parameter of the fan 200 according to the sleeping wind control curve.

Figure 2:
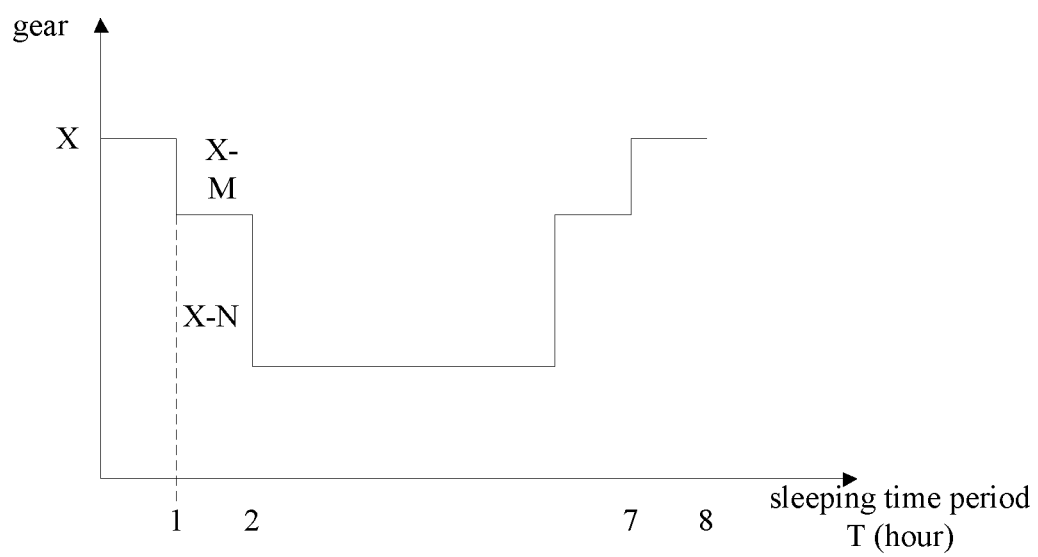
FIG. 2 is a schematic diagram illustrating a sleeping wind control curve according to an embodiment of the present disclosure.

In an embodiment of the present disclosure, as illustrated in FIG. 2, the operation parameter includes an operation gear and a rotation angle. The sleeping wind control curve is a curve representing a correspondence relationship between sleeping time periods and operation gears.

The sleeping wind control curve is generated based on a basic reference variable, which is a preset gear X of the fan 200 before the user enters the sleeping state. The fan may rotate according to a preset rotation angle when the fan adjusts an operation gear according to the sleeping wind control curve. The preset rotation angle may be defaulted to 90°.

In detail, as illustrated in FIG. 2, when the fan 200 receives the sleeping wind mode instruction sent from the wearable device 100, the fan 200 may automatically operate according the sleeping wind control curve, that is, the fan 200 may adjust the operation gear according to the sleeping wind control curve and rotate according to the preset rotation angle, such as 90°. X is the preset gear of the fan 200 before the user enters the sleeping state, which is set according to self-demand of the user. M and N may be preset according to actual situation. For example, M may be set as 2, and N may be set as 5. If X−M or X−N is less than or equal to 0, a corresponding operation gear is defaulted to 1.

It should be noted that, when the fan 200 is controlled, by the wearable device 100, to enter the sleeping wind mode, automatically operating according to the sleeping wind control curve is starting to adjust the operation gear of the fan 200 from a gear of X−M. The user may set the rotation angle of the fan 200 via a button, a remote control, a mobile terminal and the like, and turn on or off the rotation function.

In another embodiment of the present disclosure, when the user does not wear the wearable device 100, the user may directly control the fan 200 to enter the sleeping wind mode via a button, a remote control, a mobile terminal and the like. The remote control may communicate with the fan via wireless communication modes such as infrared, radio frequency, WIFI, etc. When the fan 200 enters the sleeping wind mode, the fan 200 operates at the preset gear X for 1 hour first, then the operation gear of the fan 200 is adjusted from gear X−M. After the fan 200 operates for 8 hours, the fan continues to operate at the preset gear X.

In yet another embodiment of the present disclosure, when the fan 200 does not receive the sleeping wind mode instruction, the fan 200 operates at the preset gear X.

In an embodiment of the present disclosure, when the wearable device 100 is configured to start a timer when detecting that the user wakes up from the sleeping state, to generate an exit instruction when a time period recorded by the timer reaches a preset time period, and to send the exit instruction to the fan 200, such that the fan 200 exits the sleeping wind mode.

In detail, when the wearable device 100 detects that the user wakes up from the sleeping state. A time period in which the user is in an awaking state is accumulated. When the accumulated time period in which the user is in an awaking state is greater than the preset time period, the wearable device 100 generates the exit instruction, and sends the exit instruction to the fan 200, such that the fan 200 exits the sleeping wind mode according to the exit instruction. When the accumulated time period in which the user is in an awaking state is smaller than or equal to the preset time period, the wearable device 100 may determine that the user performs an active behavior in a short awake state during the sleeping state during sleep, for example, a behavior such as going to the restroom, drinking water, or the like, and the wearable device 100 does not act.

Further, after the fan 200 exits the sleeping wind mode, the fan 100 may enter a monitoring mode, or a normal wind mode. The monitoring mode may be understood as a standby mode. At this time, the user may send a control instruction to the fan 200 through the button, the remote control, the mobile terminal or the like. After the fan 200 receives the control instruction, the fan enters corresponding work mode. A gear of the fan corresponding to the normal wind mode may be the preset gear X.

In an embodiment of the present disclosure, when the communication connection between the wearable device 100 and the fan 200 is disconnected, the fan 200 is automatically turned off. When the communication connection between the wearable device 100 and the fan 200 is re-established, the fan 200 is automatically turned on.

In detail, when a distance between the wearable device 100 and the fan 200 is relative far, the communication connection wearable device 100 and the fan 200 may not be established, which may be defined as a leaving home mode, at this time, the fan 200 is automatically turned off. When the distance between the wearable device 100 and the fan 200 is relative near, the communication connection wearable device 100 and the fan 200 may be automatically established, which may be defined as returning home mode, at this time the fan 200 may be automatically turned on. For example, when the user leaves home, the communication connection between the wearable device 100 and the fan 200 is disconnected, when a time period for the disconnection reaches 10 minutes, the fan 200 is automatically turned off. When the user comes back home, the communication connection between the wearable device 100 and the fan 200 is re-established, and the fan 200 is automatically turned on at once.

Figure 3:
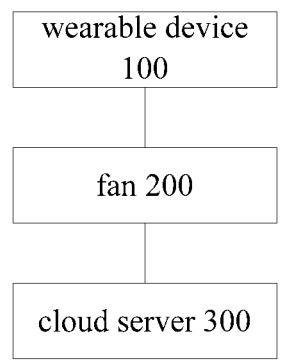
FIG. 3 is a block diagram illustrating a fan control system according to another embodiment of the present disclosure.

In an embodiment of the present disclosure, as illustrated in FIG. 3, the above mentioned fan control system may further include a cloud server 300. The cloud server 300 is configured to communicate with the fan 200. The fan 200 is configured to send an operation parameter each time the fan enters the sleeping wind mode to the cloud server 300. The cloud server 300 is configured to modify the sleeping wind control curve according to the operation parameter, and to send the modified sleeping wind control curve to the fan 200.

In detail, the fan 200 may establish a communication connection with the cloud server 300 through internet. The fan 200 sends, during a period of time, the operation parameter each time the fan enters the sleeping wind mode to the cloud server 300. The cloud server 300 obtains a sleeping habit of the user by analyzing and computing the operation parameter, and modifies the sleeping wind control curve according to the sleeping habit of the user. When the fan 200 operates according to the sleeping wind control curve again, the cloud server 300 automatically updates the modified sleeping wind control curve to the fan 200, and modifies the preset gear X, for example, selecting a preset gear commonly used by the user in a most recent time period. Thus, the sleeping wind control curve may be more satisfied with the needs of the user, and the user experience is improved.

In an embodiment of the present disclosure, the wearable device 100 is further configured to generate a wind speed adjusting instruction according to the body parameter of the user, and to send the wind speed adjusting instruction to the fan 200 to adjust an outlet wind speed of the fan. The body parameter may include body temperature, expression, irritability, a sleeping state, and the like. The outlet wind speed of the fan 200 is finely adjusted based on the body parameters of the user, so that the outlet wind speed of the fan is more suitable for the actual situation of the user, and the user's comfort is improved.

Figure 4:
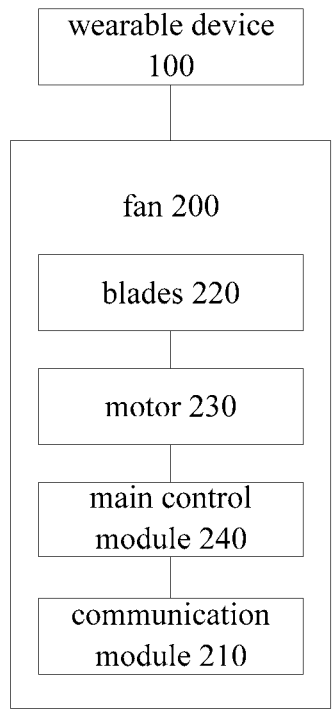
FIG. 4 is a block diagram illustrating a fan control system according to yet another embodiment of the present disclosure.

In an embodiment of the present disclosure, as illustrated in FIG. 4, the fan may include: a communication module 210, blades 220, a motor 230, and a main control module 240. The communication module 210 is configured to establish a communication connection with the wearable device 100. The motor 230 is configured to drive the blades to rotate. The main control module 240 is configured to control an operation mode of the fan 200, and to control a rotation speed of the motor 230 according to the operation mode of the fan 200.

With the fan control system according to embodiments of the present disclosure, the wearable device detects the body parameter of the user to determine whether the user enters the sleeping state, generates the sleeping wind mode instruction when the user enters the sleeping state, and the sleeping wind mode instruction is sent to the fan, the fan enters the sleeping wind mode after receiving the sleeping wind mode instruction, the sleeping wind control curve is obtained, and the operation parameter is adjusted according to the sleeping wind control curve. Thereby, the system may adjust an operation gear of the fan according to the sleeping wind control curve when the user enters the sleeping state, without interference factors, thus improving control accuracy of the fan, and improving the user experience.

Figure 5:
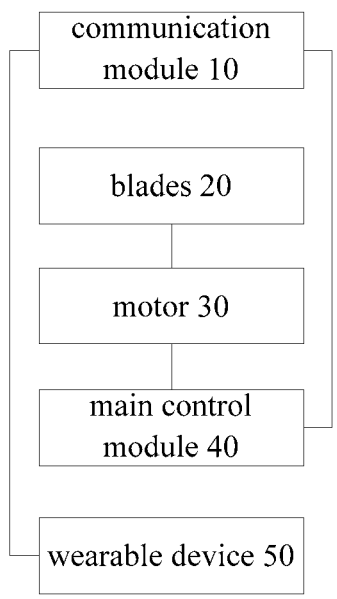
FIG. 5 is a block diagram illustrating a fan according to an embodiment of the present disclosure.

FIG. 5 is a block diagram illustrating a fan according to an embodiment of the present disclosure. As illustrated in FIG. 5, the fan includes a communication module 10, blades 20, a motor 30, and a main control module 40.

In detail, the communication module is configured to establish a communication connection with a wearable device 50 to receive a sleeping wind mode instruction sent by the wearable device 50. The wearable device 50 is configured to detect a body parameter of a user to determine whether the user is in a sleeping state, and to generate the sleeping wind mode instruction when the user is in the sleeping state. The motor 30 is configured to drive the blades 20 to rotate. The main control module 40 is configured to control the fan to enter a sleeping wind mode when the communication module 10 receives the sleeping wind mode instruction, to obtain a sleeping wind control curve, and to adjust an operation parameter of the fan according to the sleeping wind control curve.

In detail, in some embodiments of the present disclosure, the wearable device 50 may determine whether the user enters the sleeping state by detecting a current heart rate and exercise parameter information of the user. For example, the wearable device 50 may determine whether the user enters the sleeping state by detecting a heart rate and exercise parameter information in 20 minutes of the user. If it is determined that the user enters the sleeping state, the wearable device 50 generates the sleeping wind mode instruction, and sends the sleeping wind mode instruction to the communication module 10. When a distance between the fan 200 and the wearable device 50 is relative small, for example, 10 meters, the communication module 10 and the wearable device 50 may perform communication through Bluetooth, WiFi, and the like. After the communication module 10 receives the sleeping wind mode instruction sent from the wearable device 50, the main control module 40 is configured to control the fan to enter the sleeping wind mode, to obtain the sleeping wind control curve, and to adjust the operation parameter of the fan according to the sleeping wind control curve.

In addition, in an embodiment of the present disclosure, the communication module 10 is further configured to receive a gear setting instruction sent from a remote control or the wearable device 50. The main control module 40 is configured to control the fan to operate at a preset gear according to the gear setting instruction.

In an embodiment of the present disclosure, as illustrated in FIG. 2, the operation parameter includes an operation gear and a rotation angle. The sleeping wind control curve is a curve representing a correspondence relationship between sleeping time periods and operation gears. The sleeping wind control curve is generated based on a basic reference variable, which is a preset gear of the fan before the user enters the sleeping state. The fan may rotate according to a preset rotation angle when the fan adjusts an operation gear according to the sleeping wind control curve. The preset rotation angle may be defaulted to 90°.

In detail, as illustrated in FIG. 2, when the communication module 10 receives the sleeping wind mode instruction sent from the wearable device 50, the main control module 40 may automatically control the fan to operate according the sleeping wind control curve, that is, the main control module 40 may adjust the operation gear according to the sleeping wind control curve and rotate according to the preset rotation angle, such as 90°. X is the preset gear of the fan 300 before the user enters the sleeping state, which is set according to self-demand of the user. M and N may be preset according to actual situation. For example, M may be set as 2, and N may be set as 5. If X−M or X−N is less than or equal to 0, a corresponding operation gear is defaulted to 1.

It should be noted that, when the fan is controlled, by the wearable device 50, to enter the sleeping wind mode, the main control module 40 automatically controls the fan to operate according to the sleeping wind control curve is starting to adjust the operation gear of the fan from a gear of X−M. The user may set the rotation angle of the fan 200 via a button, a remote control, a mobile terminal and the like, and turn on or off the rotation function.

In another embodiment of the present disclosure, when the user does not wear the wearable device 50, the user may directly control the fan to enter the sleeping wind mode via a button, a remote control, a mobile terminal and the like. The remote control may communicate with the communication module 10 of the fan via wireless communication modes such as infrared, radio frequency, WIFI, etc. When the fan enters the sleeping wind mode, the main control module 40 operates at the preset gear X for 1 hour first, then the operation gear of the fan is adjusted from gear X−M. After the fan operates for 8 hours, the fan continues to operate at the preset gear X.

In some embodiments of the present disclosure, when the communication module 10 does not receive the sleeping wind mode instruction, the main control module controls the fan to operate at the preset gear X.

In an embodiment of the present disclosure, when the wearable device 50 is configured to start a timer when detecting that the user wakes up from the sleeping state, to generate an exit instruction when a time period recorded by the timer reaches a preset time period, and to send the exit instruction to the communication module 10. The main control module 40 is configured to control the fan to exit the sleeping wind mode according to the exit instruction. The preset time period may be set according to practical situation.

In detail, when the wearable device 50 detects that the user wakes up from the sleeping state. A time period in which the user is in an awaking state is accumulated. When the accumulated time period in which the user is in an awaking state is greater than the preset time period, the wearable device 50 generates the exit instruction, and sends the exit instruction to the communication module 10, and the main control module 40 controls the fan to exit the sleeping wind mode according to the exit instruction. The preset time period may be set according to practical situation. When the accumulated time period in which the user is in an awaking state is smaller than or equal to the preset time period, the wearable device 50 may determine that the user performs an active behavior in a short awake state during the sleeping state during sleep, for example, an behavior such as going to the restroom, drinking water, or the like, and the wearable device 50 does not act.

Further, after the fan exits the sleeping wind mode, the fan may enter a monitoring mode, or a normal wind mode. The monitoring mode may be understood as a standby mode. At this time, the user may send a control instruction to the communication module 10 through the button, the remote control, the mobile terminal or the like. After the communication module 10 receives the control instruction, the main control module 40 controls the fan to enter corresponding work mode. A gear of the fan corresponding to the normal wind mode may be the preset gear X.

In an embodiment of the present disclosure, the main control module 40 is configured to control the fan to turn off automatically when communication connection between the wearable device and the fan is disconnected. The main control module 40 is configured to control the fan to turn on automatically turned on when the communication connection between the wearable device 50 and the fan is re-established.

In detail, when a distance between the wearable device 50 and the fan is relative far, the communication connection wearable device 50 and the communication module 10 may not be established, which may be defined as a leaving home mode, at this time, the main control module 40 controls the fan to be automatically turned off. When the distance between the wearable device 50 and the fan is relative near, the communication connection wearable device 50 and the communication module 10 may be automatically established, which may be defined as returning home mode, at this time the main control module 40 controls the fan to be automatically turned on. For example, when the user leaves home, the communication connection between the wearable device 50 and the communication module 10 is disconnected, when a time period for the disconnection reaches 10 minutes, the main control module 40 controls the fan 200 to be automatically turned off. When the user comes back home, the communication connection between the wearable device 50 and the communication module 10 is re-established, and the main control module 40 controls the fan 200 to be automatically turned on at once.

In an embodiment of the present disclosure, the fan is further configured to communicate with a cloud server through the communication module 10. The fan sends an operation parameter each time the fan enters the sleeping wind mode to the cloud server. The cloud server is configured to modify the sleeping wind control curve according to the operation parameter, and to send the modified sleeping wind control curve to the fan.

In detail, the communication module 10 may establish a communication connection with the cloud server through internet. The fan sends, during a period of time, the operation parameter each time the fan enters the sleeping wind mode to the cloud server. The cloud server obtains a sleeping habit of the user by analyzing and computing the operation parameter, and modifies the sleeping wind control curve according to the sleeping habit of the user. When the main control module 40 controls the fan to operate according to the sleeping wind control curve again, the cloud server automatically updates the modified sleeping wind control curve to the fan, and modifies the preset gear X, for example, selecting a preset gear commonly used by the user in a most recent time period. Thus, the sleeping wind control curve may be more satisfied with the needs of the user, and the user experience is improved.

In an embodiment of the present disclosure, the wearable device 50 is further configured to generate a wind speed adjusting instruction according to the body parameter of the user, and to send the wind speed adjusting instruction to the communication module 10. The main control module 40 adjusts a rotation speed of the motor to adjust an outlet wind speed of the fan. The body parameter may include body temperature, expression, irritability, a sleeping state, and the like. The outlet wind speed of the fan is finely adjusted based on the body parameters of the user, so that the outlet wind speed of the fan is more suitable for the actual situation of the user, and the user's comfort is improved.

With the fan according to embodiments of the present disclosure, communication connection with the wearable device is established by the communication module to receive the sleeping wind mode instruction sent from the wearable device, controls the fan is controlled by the main control module to enter the sleeping wind mode when the communication module receives the sleeping wind mode instruction, the sleeping wind control curve is obtained, and the operation parameter is adjusted according to the sleeping wind control curve. Thereby, the fan may adjust an operation gear of the fan according to the sleeping wind control curve when the user enters the sleeping state, without interference factors, thus improving control accuracy of the fan, and improving the user experience.

Figure 6:
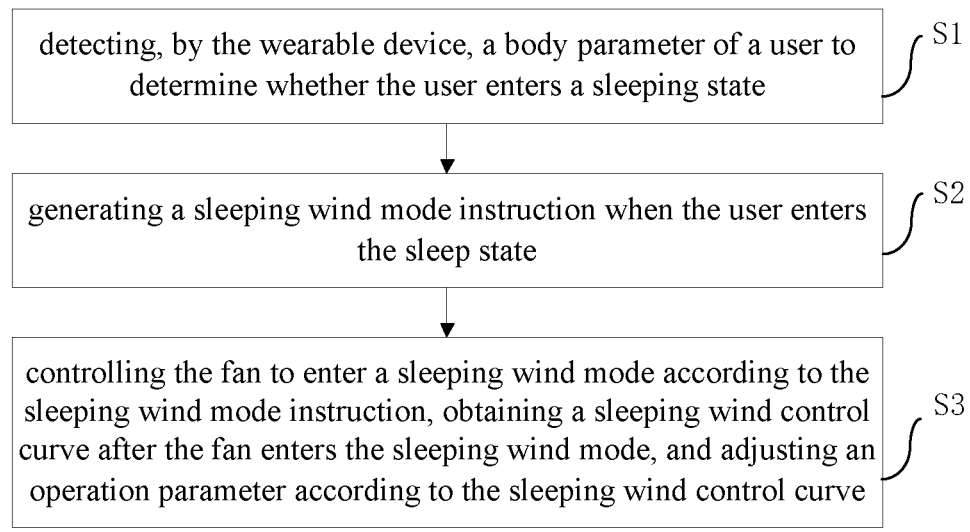
FIG. 6 is a flow chart of a control method of a fan according to an embodiment of the present disclosure.

FIG. 6 is a flow chart of a control method of a fan according to an embodiment of the present disclosure. As illustrated in FIG. 6, the control method of a fan includes follows.

At block S1, a wearable device detects a body parameter of a user to determine whether the user enters a sleeping state.

At block S2, a sleeping wind mode instruction is generated when the user enters the sleeping state.

At block S3, the fan is controlled to enter a sleeping wind mode according to the sleeping wind mode instruction, a sleeping wind control curve is obtained after the fan enters the sleeping wind mode, and an operation parameter is adjusted according to the sleeping wind control curve.

In detail, in some embodiments of the present disclosure, the wearable device may determine whether the user enters the sleeping state by detecting a current heart rate and exercise parameter information of the user. For example, the wearable device may determine whether the user enters the sleeping state by detecting a heart rate and exercise parameter information in 20 minutes of the user. If it is determined that the user enters the sleeping state, the wearable device generates the sleeping wind mode instruction, and sends the sleeping wind mode instruction to the fan. When a distance between the fan and the wearable device is relative small, for example, 10 meters, the fan and the wearable device may perform communication through Bluetooth, WiFi, and the like. After receiving the sleeping wind mode instruction sent from the wearable device, the fan automatically enters the sleeping wind mode. The fan obtains the sleeping wind control curve, and adjusts the operation parameter of the fan according to the sleeping wind control curve.

In an embodiment of the present disclosure, as illustrated in FIG. 2, the operation parameter includes an operation gear and a rotation angle. The sleeping wind control curve is a curve representing a correspondence relationship between sleeping time periods and operation gears. The sleeping wind control curve is generated based on a basic reference variable, which is a preset gear of the fan before the user enters the sleeping state. The fan may rotate according to a preset rotation angle when the fan adjusts an operation gear according to the sleeping wind control curve. The preset rotation angle may be defaulted to 90°.

In detail, as illustrated in FIG. 2, when the fan receives the sleeping wind mode instruction sent from the wearable device, the fan may automatically operate according the sleeping wind control curve, that is, the fan may adjust the operation gear according to the sleeping wind control curve and rotate according to the preset rotation angle, such as 90°. X is the preset gear of the fan before the user enters the sleeping state, which is set according to self-demand of the user. M and N may be preset according to actual situation. For example, M may be set as 2, and N may be set as 5. If X−M or X−N is less than or equal to 0, a corresponding operation gear is defaulted to 1.

It should be noted that, when the fan is controlled, by the wearable device, to enter the sleeping wind mode, automatically operating according to the sleeping wind control curve is starting to adjust the operation gear of the fan from a gear of X−M. The user may set the rotation angle of the fan via a button, a remote control, a mobile terminal and the like, and turn on or off the rotation function.

In another embodiment of the present disclosure, when the user does not wear the wearable device, the user may directly control the fan to enter the sleeping wind mode via a button, a remote control, a mobile terminal and the like. The remote control may communicate with the fan via wireless communication modes such as infrared, radio frequency, WIFI, etc. When the fan enters the sleeping wind mode, the fan operates at the preset gear X for 1 hour first, then the operation gear of the fan is adjusted from gear X−M. After the fan operates for 8 hours, the fan continues to operate at the preset gear X.

In yet another embodiment of the present disclosure, when the fan does not receive the sleeping wind mode instruction, the fan operates at the preset gear X.

In an embodiment of the present disclosure, when the wearable device detects that the user wakes up from the sleeping state, a time is started. When a time period recorded by the timer reaches a preset time period, the wearable device generates an exit instruction, and sends the exit instruction to the fan, such that the fan exits the sleeping wind mode. The preset time period may be set according to practical situation.

In detail, when the wearable device detects that the user wakes up from the sleeping state. A time period in which the user is in an awaking state is accumulated. When the accumulated time period in which the user is in an awaking state is greater than the preset time period, the wearable device generates the exit instruction, and sends the exit instruction to the fan, such that the fan exits the sleeping wind mode. When the accumulated time period in which the user is in an awaking state is smaller than or equal to the preset time period, the wearable device may determine that the user performs an active behavior in a short awake state during the sleeping state during sleep, for example, a behavior such as going to the restroom, drinking water, or the like, and the wearable device does not act.

Further, after the fan exits the sleeping wind mode, the fan may enter a monitoring mode, or a normal wind mode. The monitoring mode may be understood as a standby mode. At this time, the user may send a control instruction to the fan through the button, the remote control, the mobile terminal or the like. After receiving the control instruction, the fan enters corresponding work mode. A gear of the fan corresponding to the normal wind mode may be the preset gear X.

In an embodiment of the present disclosure, when the communication connection between the wearable device and the fan is disconnected, the fan is automatically turned off. When the communication connection between the wearable device and the fan is re-established, the fan is automatically turned on.

In detail, when a distance between the wearable device and the fan is relative far, the communication connection wearable device and the fan may not be established, which may be defined as a leaving home mode, at this time, the fan is automatically turned off. When the distance between the wearable device and the fan is relative near, the communication connection wearable device and the fan may be automatically established, which may be defined as returning home mode, at this time the fan may be automatically turned on. For example, when the user leaves home, the communication connection between the wearable device and the fan is disconnected, when a time period for the disconnection reaches 10 minutes, the fan is automatically turned off. When the user comes back home, the communication connection between the wearable device and the fan is re-established, and the fan is automatically turned on at once.

In an embodiment of the present disclosure, the fan is further configured to communicate with a cloud server, and sends an operation parameter each time the fan enters the sleeping wind mode to the cloud server. The cloud server modifies the sleeping wind control curve according to the operation parameter, and sends the modified sleeping wind control curve to the fan.

In detail, the fan may establish a communication connection with the cloud server through internet. The fan sends, during a period of time, the operation parameter each time the fan enters the sleeping wind mode to the cloud server. The cloud server obtains a sleeping habit of the user by analyzing and computing the operation parameter, and modifies the sleeping wind control curve according to the sleeping habit of the user. When the fan operates according to the sleeping wind control curve again, the cloud server automatically updates the modified sleeping wind control curve to the fan, and modifies the preset gear X, for example, selecting a preset gear commonly used by the user in a most recent time period. Thus, the sleeping wind control curve may be more satisfied with the needs of the user, and the user experience is improved.

In an embodiment of the present disclosure, the wearable device generates a wind speed adjusting instruction according to the body parameter of the user, and sends the wind speed adjusting instruction to the fan to adjust an outlet wind speed of the fan. The body parameter may include body temperature, expression, irritability, a sleeping state, and the like.

The outlet wind speed of the fan is finely adjusted based on the body parameters of the user, so that the outlet wind speed of the fan is more suitable for the actual situation of the user, and the user's comfort is improved.

With the control method of a fan according to embodiments of the present disclosure, the wearable device detects the body parameter of the user to determine whether the user enters the sleeping state, the sleeping wind mode instruction is generated when the user enters the sleeping state, and the fan is controlled to enter the sleeping wind mode, the sleeping wind control curve is obtained after the fan enters the sleeping wind mode, and the operation parameter is adjusted according to the sleeping wind control curve. Thereby, the system may adjust an operation gear of the fan according to the sleeping wind control curve when the user enters the sleeping state, without interference factors, thus improving control accuracy of the fan, and improving the user experience.

In the specification, it is to be understood that terms such as "central," "longitudinal," "lateral," "length," "width," "thickness," "upper," "lower," "front," "rear," "left," "right," "vertical," "horizontal," "top," "bottom," "inner," "outer," "clockwise," "counterclockwise," "axial," "radial," and "circumferential" should be construed to refer to the orientation as then described or as shown in the drawings under discussion. These relative terms are for convenience of description and do not require that the present disclosure be constructed or operated in a particular orientation.

In addition, terms such as "first" and "second" are used herein for purposes of description and are not intended to indicate or imply relative importance or significance or to imply the number of indicated technical features. Thus, the feature defined with "first" and "second" may comprise one or more of this feature. In the description of the present disclosure, "a plurality of" means two or more than two, such as two or there, unless specified otherwise.

In the present disclosure, unless specified or limited otherwise, the terms "mounted," "connected," "coupled," "fixed" and the like are used broadly, and may be, for example, fixed connections, detachable connections, or integral connections; may also be mechanical or electrical connections; may also be direct connections or indirect connections via intervening structures; may also be inner communications of two elements, which can be understood by those skilled in the art according to specific situations.

In the present disclosure, unless specified or limited otherwise, a structure in which a first feature is "on" or "below" a second feature may include an embodiment in which the first feature is in direct contact with the second feature, and may also include an embodiment in which the first feature and the second feature are not in direct contact with each other, but are contacted via an additional feature formed there between. Furthermore, a first feature "on," "above," or "on top of" a second feature may include an embodiment in which the first feature is right or obliquely "on," "above," or "on top of" the second feature, or just means that the first feature is at a height higher than that of the second feature; while a first feature "below," "under," or "on bottom of" a second feature may include an embodiment in which the first feature is right or obliquely "below," "under," or "on bottom of" the second feature, or just means that the first feature is at a height lower than that of the second feature.

In the description of the present disclosure, reference throughout this specification to "an embodiment," "some embodiments," "an example," "a specific example," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example," "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A fan control system, comprising: a wearable device and a fan, wherein the fan and the wearable device communicate with each other,
   the wearable device is configured to detect a body parameter of a user to determine whether the user enters a sleeping state, to generate a sleeping wind mode instruction when the user enters the sleeping state, and to send the sleeping wind mode instruction to the fan; and
   the fan is configured to enter a sleeping wind mode after receiving the sleeping wind mode instruction, to obtain a sleeping wind control curve, and to adjust an operation parameter according to the sleeping wind control curve, wherein the operation parameter comprises an operation gear and a rotation angle, the sleeping wind control curve is a curve representing a correspondence relationship between sleeping time periods and operation gears.

2. The system according to claim 1, wherein the fan operates at a preset gear when the fan does not receive the sleeping wind mode instruction.

3. The system according to claim 1, wherein the sleeping wind control curve is generated based on a basic reference variable, the basic reference variable is a preset gear of the fan before the user enters the sleeping state.

4. The system according to claim 1, wherein the fan is further configured to rotate according to a preset rotation angle when the fan adjusts an operation gear according to the sleeping wind control curve.

5. The system according to claim 1, wherein the wearable device is configured to start a timer when detecting that the user wakes up from the sleeping state, to generate an exit instruction when a time period recorded by the timer reaches a preset time period, and to send the exit instruction to the fan, such that the fan exits the sleeping wind mode.

6. The system according to claim 1, wherein, when communication connection between the wearable device and the fan is disconnected, the fan is automatically turned off; when the communication connection between the wearable device and the fan is re-established, the fan is automatically turned on.

7. The system according to claim 1, further comprising a cloud server, wherein the cloud server is configured to communicate with the fan, the fan is configured to send an operation parameter each time the fan enters the sleeping wind mode to the cloud server, the cloud server is configured to modify the sleeping wind control curve according to the operation parameter, and to send the modified sleeping wind control curve to the fan.

8. The system according to claim 1, wherein the wearable device is further configured to generate a wind speed adjusting instruction according to the body parameter of the user, and to send the wind speed adjusting instruction to the fan to adjust an outlet wind speed of the fan.

9. The system according to claim 1, wherein the fan comprises:
   a communication module, configured to establish a communication connection with the wearable device;
   blades;
   a motor, configured to drive the blades to rotate; and
   a main control module, configured to control an operation mode of the fan, and to control a rotation speed of the motor according to the operation mode of the fan.

10. A fan, comprising:
    a communication module, configured to establish a communication connection with a wearable device to receive a sleeping wind mode instruction sent by the wearable device, wherein the wearable device is configured to detect a body parameter of a user to determine whether the user is in a sleeping state, and to generate the sleeping wind mode instruction when the user is in the sleeping state;
    blades;
    a motor, configured to drive the blades to rotate; and
    a main control module, configured to control the fan to enter a sleeping wind mode when the communication module receives the sleeping wind mode instruction, to obtain a sleeping wind control curve, and to adjust an operation parameter of the fan according to the sleeping wind control curve, wherein the operation parameter comprises an operation gear and a rotation angle, the sleeping wind control curve is a curve representing a correspondence relationship between sleeping time periods and operation gears.

11. The fan according to claim 10, wherein the communication module is further configured to receive a gear setting instruction sent from the wearable device, the main control module is configured to control the fan to operate at a preset gear according to the gear setting instruction.

12. The fan according to claim 10, wherein the sleeping wind control curve is generated based on a basic reference variable, the basic reference variable is a preset gear of the fan before the user enters the sleeping state as a basic reference variable.

13. The fan according to claim 10, wherein the main control module is further configured to control the fan to rotate according to a preset rotation angle when adjusting an operation gear according to the sleeping wind control curve.

14. The fan according to claim 10, wherein the wearable device is configured to start a timer when detecting that the user wakes up from the sleeping state, to generate an exit instruction when a time period recorded by the timer reaches a preset time period, and to send the exit instruction to the communication module, the main control module is configured to control the fan to exit the sleeping wind mode according to the exit instruction.

15. The fan according to claim 10, wherein, the main control module is configured to control the fan to turn off automatically when communication connection between the wearable device and the fan is disconnected; the main control module is configured to control the fan to turn on automatically when the communication connection between the wearable device and the fan is re-established.

16. The fan according to claim 10, wherein the fan is configured to communicate with a cloud server through the communication module, and to send an operation parameter each time the fan enters the sleeping wind mode to the cloud server; the cloud server is configured to modify the sleeping wind control curve according to the operation parameter, and to send the modified sleeping wind control curve to the fan.

17. The fan according to claim 10, wherein the wearable device is further configured to generate a wind speed adjusting instruction according to the body parameter of the user, and to send the wind speed adjusting instruction to the communication module, the main control module is configured to adjust a rotation speed of the motor according to the wind speed adjusting instruction to adjust an outlet wind speed of the fan.

* * * * *